(12) United States Patent
Smith et al.

(10) Patent No.: US 7,228,176 B2
(45) Date of Patent: Jun. 5, 2007

(54) SYSTEMS, DEVICES, AND METHODS FOR TACHYARRHYTHMIA DISCRIMINATION OR THERAPY DECISIONS

(75) Inventors: Valerie Smith, Mahtomedi, MN (US); Richard Milon Dujmovic, Jr., Coon Rapids, MN (US); Julie Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 400 days.

(21) Appl. No.: 10/897,365

(22) Filed: Jul. 22, 2004

(65) Prior Publication Data

US 2006/0074330 A1    Apr. 6, 2006

(51) Int. Cl.
*A61N 1/362* (2006.01)
(52) U.S. Cl. .............................. 607/28; 607/9; 607/14
(58) Field of Classification Search ..................... None
See application file for complete search history.

(56) References Cited

U.S. PATENT DOCUMENTS

| | | | |
|---|---|---|---|
| 4,830,006 A | 5/1989 | Haluska et al. ................ 607/4 |
| 5,000,189 A | 3/1991 | Throne et al. | |
| 5,002,052 A | 3/1991 | Haluska ........................ 607/4 |
| 5,107,850 A | 4/1992 | Olive ......................... 128/705 |
| 5,161,527 A | 11/1992 | Nappholz et al. ..... 128/419 PG |
| 5,193,535 A | 3/1993 | Bardy et al. | |
| 5,193,550 A | 3/1993 | Duffin | |
| 5,205,283 A | 4/1993 | Olson | |
| 5,280,792 A | 1/1994 | Leong et al. | |
| 5,282,836 A | 2/1994 | Kreyenhagen et al. | |
| 5,311,874 A | 5/1994 | Baumann et al. | |
| 5,313,953 A | 5/1994 | Yomtov et al. | |
| 5,330,504 A | 7/1994 | Somerville et al. | |
| 5,342,402 A | 8/1994 | Olson et al. | |

(Continued)

FOREIGN PATENT DOCUMENTS

EP        253505        1/1988

(Continued)

OTHER PUBLICATIONS

MEDTRONIC, "Marquis DR 7274 Dual Chamber Implantable Cardioverter Defibrillator", Reference Manual,(Feb. 2002),426 pgs.

(Continued)

*Primary Examiner*—Carl Layno
(74) *Attorney, Agent, or Firm*—Schwegman, Lundberg, Woessner, & Kluth, P.A.

(57) ABSTRACT

This document discusses, among other things, systems, devices, and methods for detecting or classifying tachyarrhythmias or making a therapy decision. In one example, a rate-dependent threshold is used for comparing atrial and ventricular rates for classifying a tachyarrhythmia as a ventricular tachyarrhythmia (VT) or a supraventricular tachyarrhythmia (SVT). In another example, the classification uses an atrial rate cutoff value, a ventricular rate cutoff value, or both. In another example, a tachyarrhythmia detection is tested over a time window with a duration that is automatically adjusted as a substantially continuously monotonically decreasing function of duration vs. rate. These techniques improve the specificity of arrhythmia detection or classification, allow anti-tachyarrhythmia therapy to be better tailored to the particular tachyarrhythmia, or provide more automatic operation making it easier for a physician to use an implantable device.

50 Claims, 10 Drawing Sheets

U.S. PATENT DOCUMENTS

| | | | |
|---|---|---|---|
| 5,350,406 A | 9/1994 | Nitzsche et al. | |
| 5,366,487 A | 11/1994 | Adams et al. | |
| 5,379,776 A | 1/1995 | Murphy et al. | |
| 5,383,910 A | 1/1995 | den Dulk | |
| 5,447,519 A | 9/1995 | Peterson | |
| 5,462,060 A | 10/1995 | Jacobson et al. | |
| 5,513,644 A | 5/1996 | McClure et al. | |
| 5,542,430 A | 8/1996 | Farrugia et al. | |
| 5,545,186 A | 8/1996 | Olson et al. | |
| 5,549,641 A | 8/1996 | Ayers et al. | |
| 744,190 A | 11/1996 | Wilkoff | |
| 5,591,215 A | 1/1997 | Greenhut et al. | |
| 5,620,471 A | 4/1997 | Duncan | |
| 5,645,070 A | 7/1997 | Turcott | |
| 5,674,251 A | 10/1997 | Combs et al. | |
| 5,713,366 A * | 2/1998 | Armstrong et al. | 600/510 |
| 5,730,141 A | 3/1998 | Fain et al. | |
| 5,730,142 A | 3/1998 | Sun et al. | |
| 5,755,736 A | 5/1998 | Gillberg et al. | |
| 5,755,737 A | 5/1998 | Prieve et al. | |
| 5,836,975 A | 11/1998 | DeGroot | |
| 5,855,593 A | 1/1999 | Olson et al. | |
| 5,857,977 A | 1/1999 | Caswell et al. | |
| 5,873,897 A | 2/1999 | Armstrong et al. | 607/14 |
| 5,891,170 A | 4/1999 | Nitzsche et al. | 607/4 |
| 5,951,592 A | 9/1999 | Murphy | 607/4 |
| 5,968,079 A | 10/1999 | Warman et al. | |
| 5,978,707 A | 11/1999 | Krig et al. | 607/14 |
| 5,987,356 A | 11/1999 | DeGroot | |
| 5,991,656 A | 11/1999 | Olson et al. | |
| 5,991,657 A | 11/1999 | Kim | |
| 6,052,620 A | 4/2000 | Gillberg et al. | |
| 6,076,014 A | 6/2000 | Alt | |
| 6,081,745 A | 6/2000 | Mehra | |
| 6,108,578 A | 8/2000 | Bardy et al. | 607/5 |
| 6,151,524 A | 11/2000 | Krig et al. | 607/14 |
| 6,178,350 B1 | 1/2001 | Olson et al. | 607/4 |
| 6,179,865 B1 | 1/2001 | Hsu et al. | |
| 6,192,273 B1 | 2/2001 | Igel et al. | |
| 6,212,428 B1 | 4/2001 | Hsu et al. | |
| 6,223,078 B1 | 4/2001 | Marcovecchio | |
| 6,230,055 B1 | 5/2001 | Sun et al. | 607/5 |
| 6,266,554 B1 | 7/2001 | Hsu et al. | |
| 6,275,732 B1 | 8/2001 | Hsu et al. | 607/14 |
| 6,308,095 B1 | 10/2001 | Hsu et al. | |
| 6,317,632 B1 * | 11/2001 | Krig et al. | 607/14 |
| 6,438,410 B2 | 8/2002 | Hsu et al. | |
| 6,449,503 B1 | 9/2002 | Hsu | |
| 6,456,871 B1 | 9/2002 | Hsu et al. | |
| 6,484,055 B1 | 11/2002 | Marcovecchio | 607/5 |
| 6,493,579 B1 | 12/2002 | Gilkerson et al. | |
| 6,512,951 B1 | 1/2003 | Marcovecchio et al. | |
| 6,516,225 B1 | 2/2003 | Florio | 607/9 |
| 6,522,917 B1 | 2/2003 | Hsu et al. | |
| 6,658,286 B2 | 12/2003 | Seim | 600/516 |
| 6,671,548 B1 | 12/2003 | Mouchawar et al. | 607/14 |
| 6,687,540 B2 | 2/2004 | Marcovecchio | |
| 2002/0035335 A1 | 3/2002 | Schauerte | |
| 2002/0107552 A1 | 8/2002 | Krig et al. | |
| 2002/0123768 A1 | 9/2002 | Gilkerson | |
| 2002/0143370 A1 | 10/2002 | Kim | |
| 2002/0147407 A1 | 10/2002 | Seim | 600/513 |
| 2002/0147474 A1 | 10/2002 | Seim et al. | |
| 2003/0105491 A1 | 6/2003 | Gilkerson et al. | |
| 2004/0116972 A1 | 6/2004 | Marcovecchio | |
| 2005/0149125 A1 * | 7/2005 | Kim et al. | 607/5 |
| 2005/0256544 A1 | 11/2005 | Thompson | |

FOREIGN PATENT DOCUMENTS

| | | |
|---|---|---|
| EP | 360412 | 3/1990 |
| EP | 469817 | 2/1992 |
| EP | 0469817 | 2/1992 |
| EP | 597459 | 5/1994 |
| EP | 0597459 A2 | 5/1994 |
| EP | 744190 | 11/1996 |
| EP | 0879621 A2 | 11/1998 |
| EP | 919256 | 6/1999 |
| EP | 993842 | 4/2000 |
| EP | 1112756 | 7/2001 |
| WO | WO-93/02746 | 2/1993 |
| WO | WO-9739799 | 10/1997 |
| WO | WO-9825669 | 6/1998 |
| WO | WO-98/48891 | 11/1998 |
| WO | WO-9848891 | 11/1998 |
| WO | WO-98/53879 | 12/1998 |
| WO | WO-9915232 | 4/1999 |
| WO | WO-99/65570 | 12/1999 |
| WO | WO-0053089 | 9/2000 |
| WO | WO-0059573 | 10/2000 |
| WO | WO-0113993 | 3/2001 |
| WO | WO-03047690 | 6/2003 |
| WO | WO-06020198 A2 | 2/2006 |

OTHER PUBLICATIONS

"International Search Report and Written Opinion for Application No. PCT/US/2005/025397, date mailed Mar. 22, 2006", 21 Pages.

*Metrix Model 3020 Implantable Atrial Defibrillator*, Physician's Manual, InControl, Inc., Redmond, WA,(1998), pp. 4-24-4-27.

"Invitation to Pay Additional Fees for application No. PCT/US2005/025397, date mailed Dec. 16, 2005", 8 pages.

Hsu, William, "System and Method for Classifying Tachycardia Arrhythmias Having 1:1 Atrial to Ventricular Rhythms", U.S. Appl. No. 09/417,588, filed Oct. 13, 1999, 39 pgs.

Jung, J., et al., "Discrimination of Sinus Rhythm, Atrial Flutter, and Atrial Fibrillation Using Bipolar Endocardial Signals", *Journal of Cardiovascular Electrophysiology*, 9 (7), (Jul. 1998), pp. 689-695.

Swiryn, S., et al., "Detection of Atrial Fibrillation by Pacemakers and Antiarrhythmic Devices", *Nonpharmacological Management of Atrial Fibrillation*, Chapter 21, Futura Publishing Co, Inc. Armonk, NY,(1997), pp. 309-318.

* cited by examiner

US 7,228,176 B2

SYSTEMS, DEVICES, AND METHODS FOR TACHYARRHYTHMIA DISCRIMINATION OR THERAPY DECISIONS

TECHNICAL FIELD

This patent application pertains generally to cardiac rhythm management and more particularly, but not by way of limitation, to systems, devices, and methods for discriminating between ventricular and supraventricular tachyarrhythmias.

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a patient. For example, a tachyarrhythmia includes a too-fast heart rhythm. A tachyarrhythmia may be caused by an improper positive-feedback-like reentry of intrinsic electrical signals that control heart contractions. A tachyarrhythmia may result in inefficient pumping of blood. Fibrillation is a particularly severe tachyarrhythmic episode. While ventricular fibrillation ("VF") can have immediate life-threatening consequences, the adverse effects of atrial fibrillation ("AF") are typically less immediate or severe. Atrial tachyarrhythmias (i.e., "AT"s, including AF) may call for a different therapy than ventricular tachyarrhythmias (i.e., "VT"s). For example, a VF may call for delivering a painful defibrillation shock to interrupt the VF, while an AF may call for delivering a painless anti-tachyarrhythmia pacing to interrupt the AF. Therefore, to promote efficacy or patient comfort, it is useful to know whether a particular tachyarrhythmia originates in the ventricle (i.e., is a VT) or above the ventricle (i.e., is a supraventricular tachyarrhythmia ("SVT"), such as an AT).

However, it is sometimes difficult to know where the tachyarrhythmia originates. A SVT may conduct its too-fast heart rhythm through the atrioventricular (AV) node to the ventricle, resulting in a fast ventricular heart rate. Similarly, a VT may exhibit retrograde conduction of its too-fast heart rhythm back to the atrium, resulting in a fast atrial heart rate. Thus, discriminating between the different origins of VTs and SVTs may not be an easy task. Accomplishing this VT/SVT discrimination task may require a physician to program a complicated set of parameters to achieve the intended result. The present inventors have recognized an unmet need for automatically or otherwise providing improved sensitivity and specificity of discriminating between VTs and SVTs, such as to avoid unneeded defibrillation shocks and to more effectively treat the particular tachyarrhythmia.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

This detailed description includes references to accompanying drawings, which form a part of the detailed description. The drawings illustrate specific embodiments of practicing the invention. These embodiments, which are also referred to herein as "examples," are described in enough detail to enable those skilled in the art to practice the invention. The embodiments may be combined, other embodiments may be utilized, or structural, logical, and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
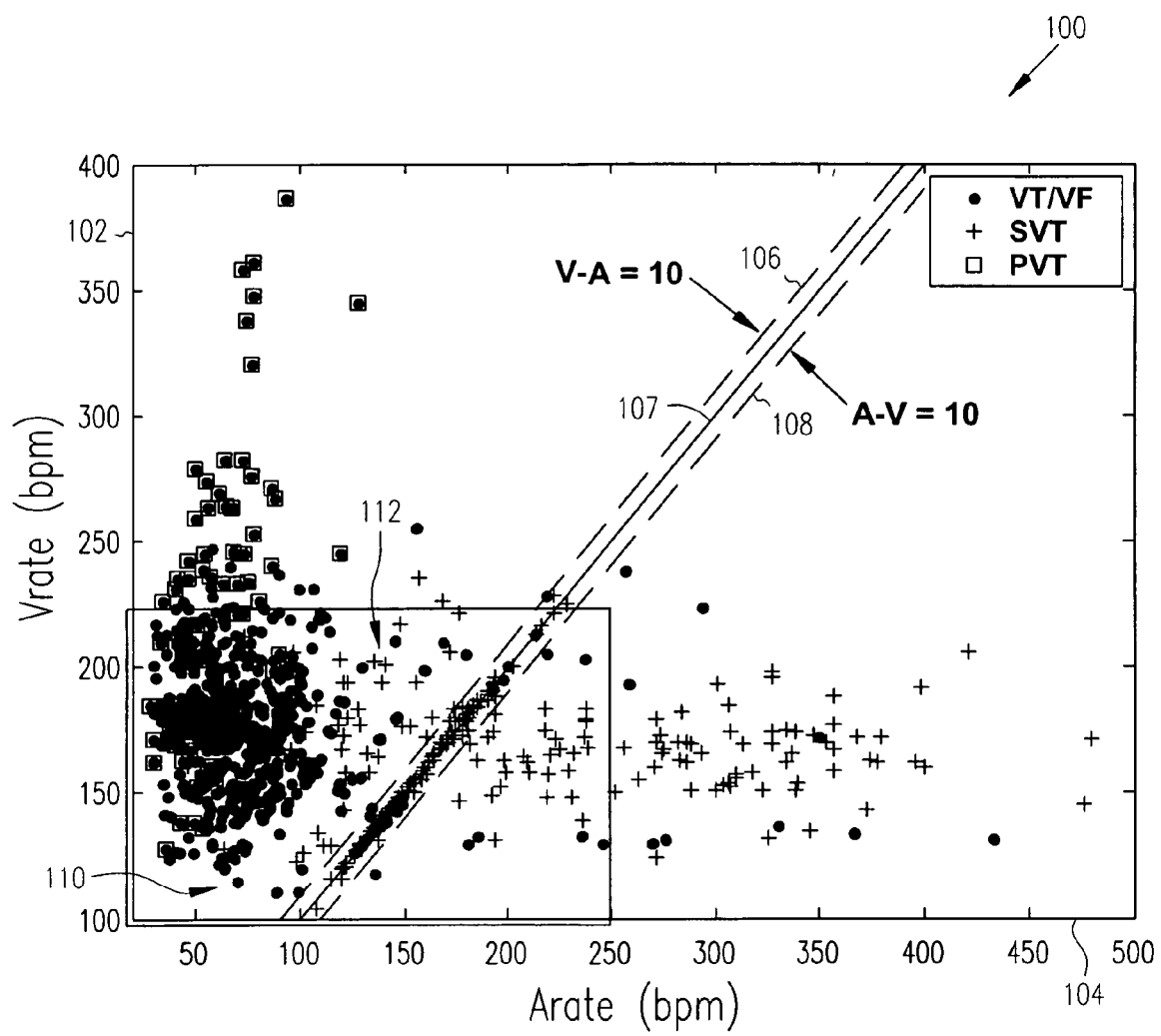
FIG. 1 is a graph of data illustrating tachyarrhythmia episodes from different patients.

FIG. 1 is a graph 100 of data illustrating tachyarrhythmia episodes from different patients, as collected and analyzed by the present inventors. The graph of FIG. 1 includes a y-axis 102 that illustrates ventricular rate (in beats per minute), and an x-axis 104 that illustrates atrial rate (in beats per minute). In FIG. 1, each VT (including VF) episode is indicated by a bullet (•) and each SVT (including AF) episode is indicated by a plus (+). Each polymorphic VT episode is illustrated by a box (?) around the corresponding bullet. A VT episode indicated by a bullet without a corresponding box is a monomorphic VT episode. A monomorphic VT episode has a more regular morphology (i.e., shape) of intrinsic heart signal than a polymorphic VT episode. A monomorphic VT episode may call for a different anti-tachyarrhythmia therapy than a polymorphic VT episode.

In FIG. 1, a line with a slope of +0.5 and intersecting the (extrapolated) y-axis 102 at y=0 defines an atrial rate ("AR") that is equal to a ventricular rate ("VR"). As seen in FIG. 1, most VT episodes correspond to VR>AR. Similarly, most SVT episodes correspond to AR>VR. Therefore, one way to distinguish between a VT episode and an SVT episode in an implantable medical device is to include an algorithm that compares AR and VR. If VR>AR by a desired threshold value (e.g., 10 bpm), then the algorithm deems the detected arrhythmia to be a VT. In FIG. 1, this corresponds to episodes to the left of line 106. In this example, if AR>VR by the same or a different threshold value (e.g., 10 bpm), then the algorithm deems the detected arrhythmia to be an SVT. In FIG. 1, this corresponds to episodes to the right of line 108. If both desired threshold values are set to zero, this reduces to classifying episodes to the left of the AR=VR line as VTs and classifying the episodes to the right of the AR=VR line as SVTs. If desired, anti-tachyarrhythmia therapy can be tailored to the particular tachyarrhythmia using this information, and delivered to the patient.

Figure 2:
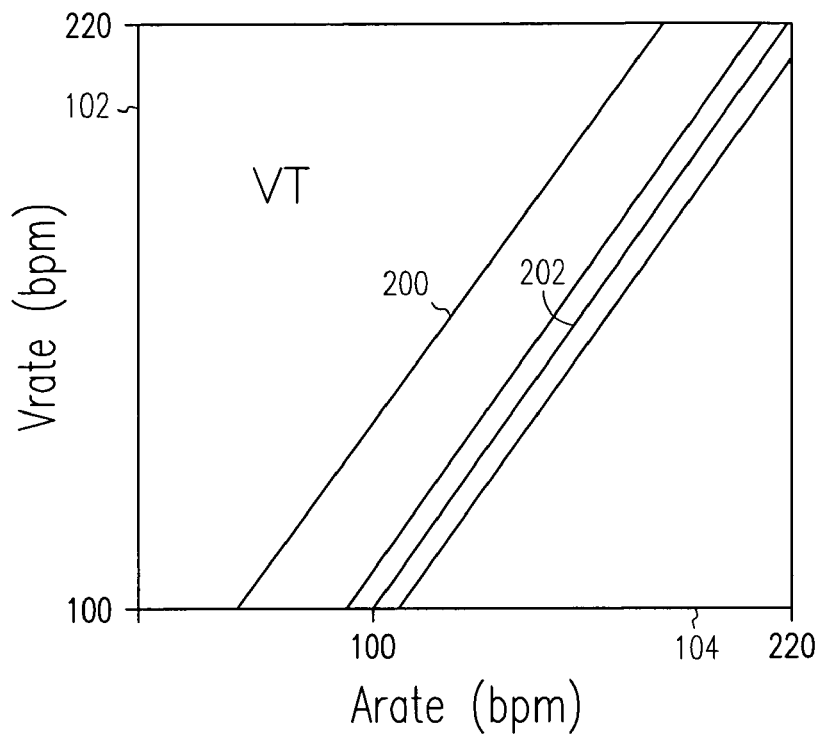
FIG. 2 is a graph illustrating conceptually one example of using a fixed rate threshold for comparing atrial and ventricular rates, such as for classifying a tachyarrhythmia as a ventricular tachyarrhythmia.

However, in FIG. 1, there are fewer VTs at lower ventricular rates, such as in region 110, than at higher ventricular rates. Also, in FIG. 1, there are fewer VTs, and more SVTs where the atrial rate exceeds an atrial rate cutoff value (e.g., at an AR that is somewhere between about 100 bpm and 200 bpm), such as in region 112. Among other things, the present inventors have recognized that using a substantially larger fixed threshold for the comparison (e.g., VR>>AR by a fixed threshold value of at least about 40 bpm to about 60 bpm, instead of the 10 bpm depicted by the line 106 in FIG. 1) would improve the specificity of classifying a tachyarrhythmia as VT. This is illustrated by the boundary line 200 in the graph of FIG. 2. The threshold value for the comparison is shown as the distance between the boundary line 200 in FIG. 2 and a VR=AR line 202 having slope=0.5 and y-intercept=0.

Moreover, the present inventors have recognized that instead of using a fixed threshold for comparing AR and VR (e.g., a threshold represented on FIG. 1 by a boundary line having a fixed distance from an AR=VR line 107 having slope of 0.5 and y-intercept of 0), using an atrial or ventricular rate dependent or other variable threshold may add power to the VT/SVT discrimination and classification algorithm, thereby improving its sensitivity or specificity.

Figure 3:
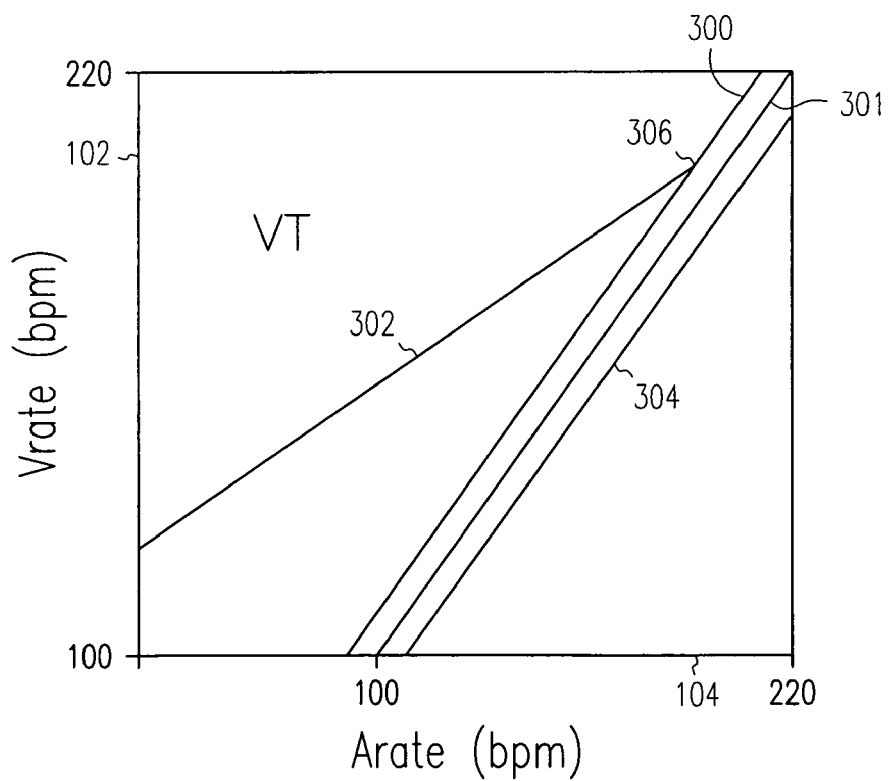
FIG. 3 is a graph illustrating a rate-dependent comparison threshold, such as illustrated by a bilinear, piecewise linear, curvilinear, or other nonlinear threshold boundary.

FIG. 3 is a graph illustrating a rate-dependent comparison threshold, such as illustrated by a bilinear, piecewise linear, curvilinear, or other nonlinear threshold boundary 300 in the context of the graph of FIG. 3. (In examples illustrated in graphs such as shown in FIG. 3, the actual threshold value for comparing AR and VR is the distance between the threshold boundary 300 and the AR=VR line 301 illustrated in FIG. 3.)

In the example of FIG. 3, the threshold boundary 300 is such that, for an arrhythmia to be classified as a VT, VR must exceed AR by a greater threshold amount at lower values of VR than at higher values of VR. In other words, the distance between the threshold boundary 300 and the AR=VR line 301 is greater at lower values of VR than at higher values of VR. Similarly, the distance between the threshold boundary 300 and the AR=VR line 301 is greater at lower values of AR than at higher values of AR.

The example of FIG. 3 depicts a bilinear threshold boundary 300, formed by the line segments 302 and 304, which are joined at breakpoint 306. In this example, the line segment 302, at lower values of VR and AR, is rate dependent (because its slope is not equal to 0.5) and the line segment 304, at higher values of VR and AR is rate independent (because its slope is equal to 0.5). Therefore, in its entirety, the threshold boundary 300 can be considered rate dependent because at least a portion of it (i.e., line segment 302) is rate dependent.

Figure 4:
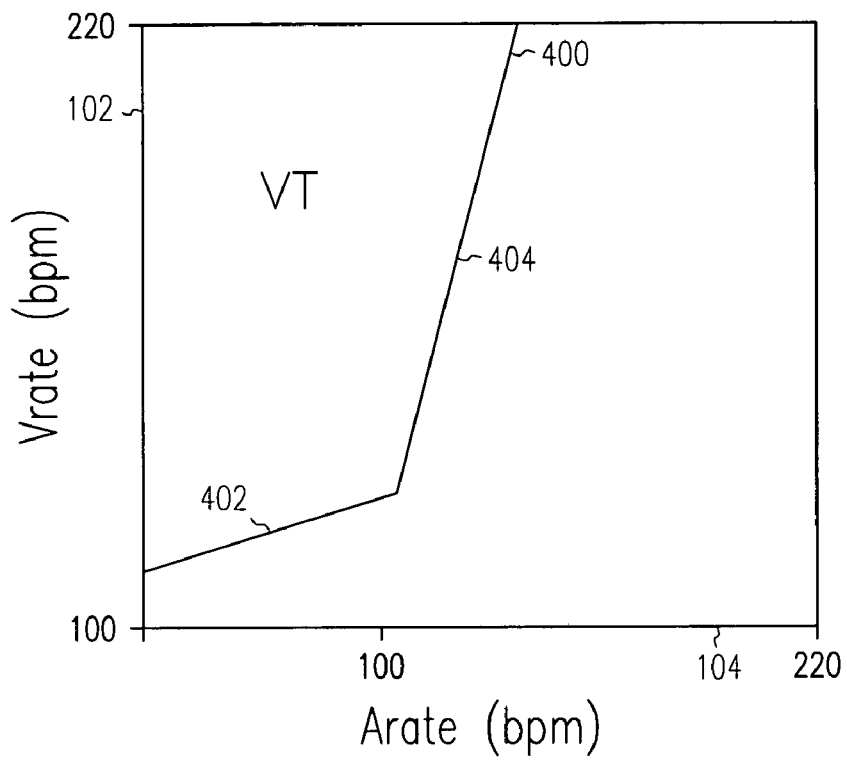
FIG. 4 is a graph that illustrates an alternative example in which a bilinear threshold boundary includes a line segment that has a slope that is less than 0.5, and line segment that has a slope that is greater than 0.5.

In the example of FIG. 3, the breakpoint 306 is located at about VR=180 bpm and AR=170 bpm, however, FIG. 3 is merely exemplary and is drawn to emphasize the conceptual nature of the rate dependent threshold as represented by a threshold boundary. The exact location of the breakpoint 306 or the slope of line segment 302 is typically determined using data (such as shown in FIG. 1) along with a desired specificity of classifying the arrhythmia as a VT. Moreover, the line segment 304 need not be rate independent (e.g., slope=0.5), but may also be rate dependent. FIG. 4 is a graph that illustrates an alternative example in which a bilinear threshold boundary 400 includes a line segment 402 that has a slope that is less than 0.5, and line segment 404 that has a slope that is greater than 0.5.

Figure 5:
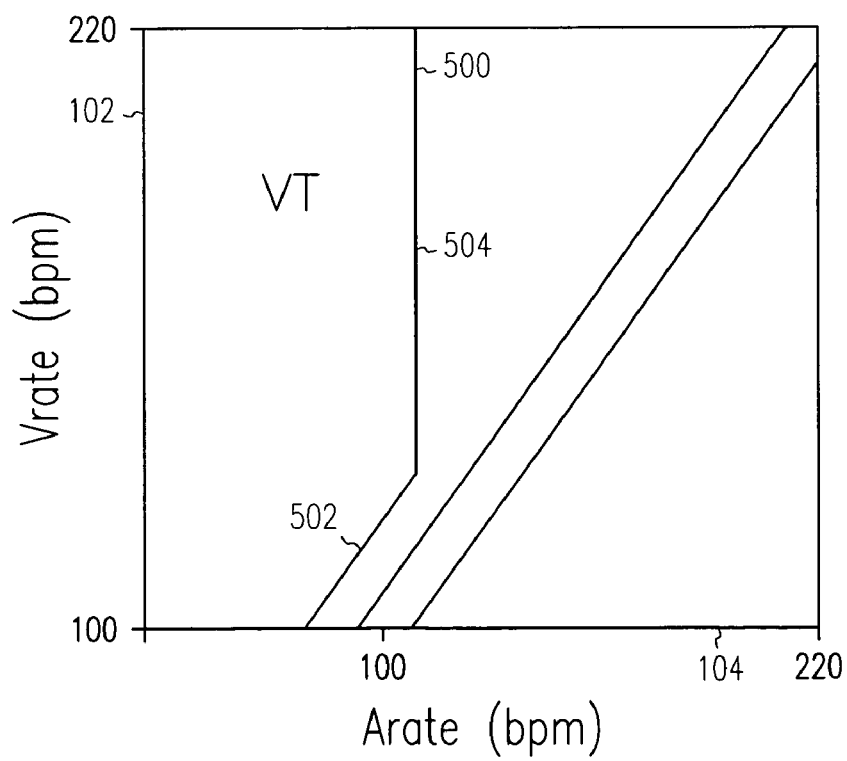
FIG. 5 is a graph illustrating an alternative example of a bilinear threshold boundary comprising a lower rate line segment, and a higher rate line segment that has substantially infinite slope, such as to implement an atrial rate cutoff value.

FIG. 5 is a graph illustrating an alternative example of a bilinear threshold boundary 500 comprising a lower rate line segment 502 and a higher rate line segment 504. In this example, the higher rate line segment 504 has substantially infinite slope, as illustrated in FIG. 5. This effectively implements an atrial rate cutoff value, such as by extrapolating the line segment 504 to the corresponding atrial rate on the x-axis 104. In this example, an arrhythmia occurring at an observed AR greater than the atrial rate cutoff value (e.g., about 110 bpm, in the example illustrated in FIG. 4) will not be classified as a VT, regardless of the VR value observed during that arrhythmia. Although the line segment 502 is shown in FIG. 5 as being rate independent (i.e., slope=0.5), it could also be made rate dependent (for example, slope less than 0.5).

Figure 6:
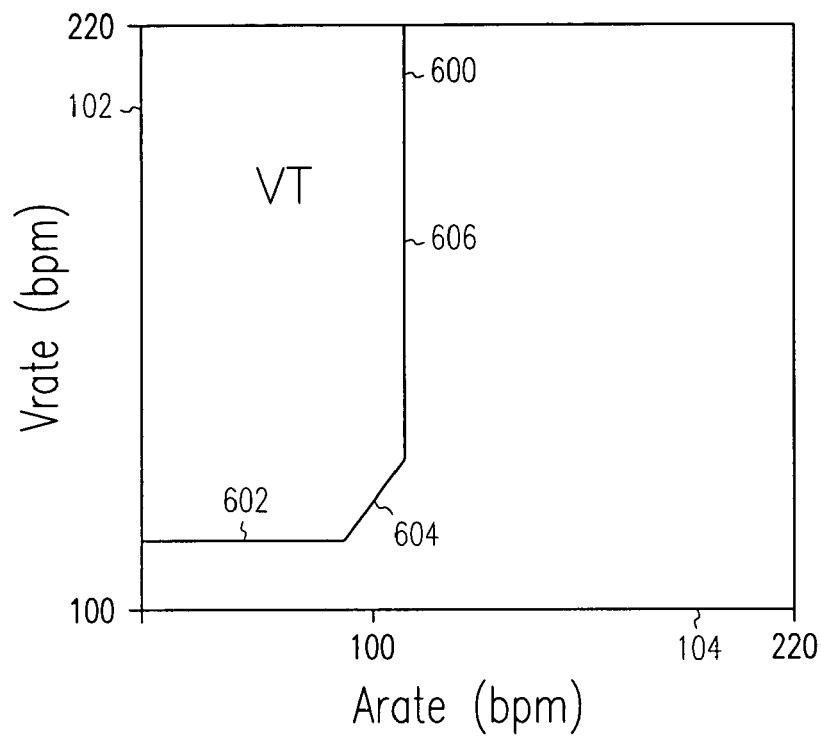
FIG. 6 is a graph illustrating an alternative example in which the rate-dependent threshold boundary is piecewise linear, such as by including more than two line segments.

FIG. 6 is a graph illustrating an alternative example in which the rate-dependent threshold boundary 600 is piecewise linear, such as by including more than two line segments. In the example of FIG. 6, the rate dependent threshold boundary 600 includes three line segments 602, 604, and 606, having slopes of 0, 0.5, and 8, respectively, although other slopes or breakpoints are also contemplated.

Figure 7:
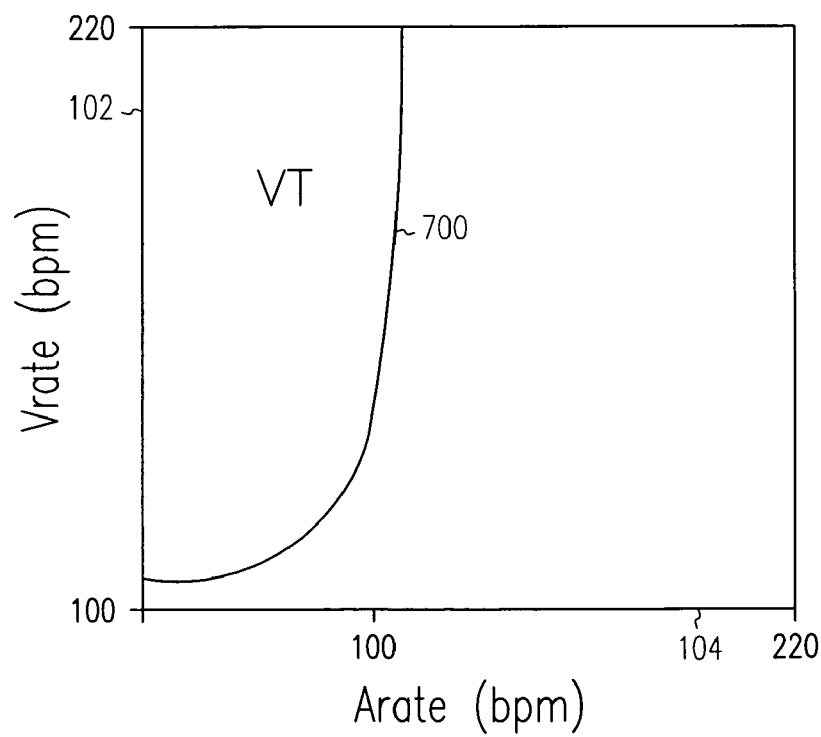
FIG. 7 is a graph illustrating an alternative example in which the rate dependent threshold boundary is curvilinear.

FIG. 7 is a graph illustrating an alternative example in which the rate dependent threshold boundary 700 is not piecewise linear, but is instead curvilinear.

Figure 8:
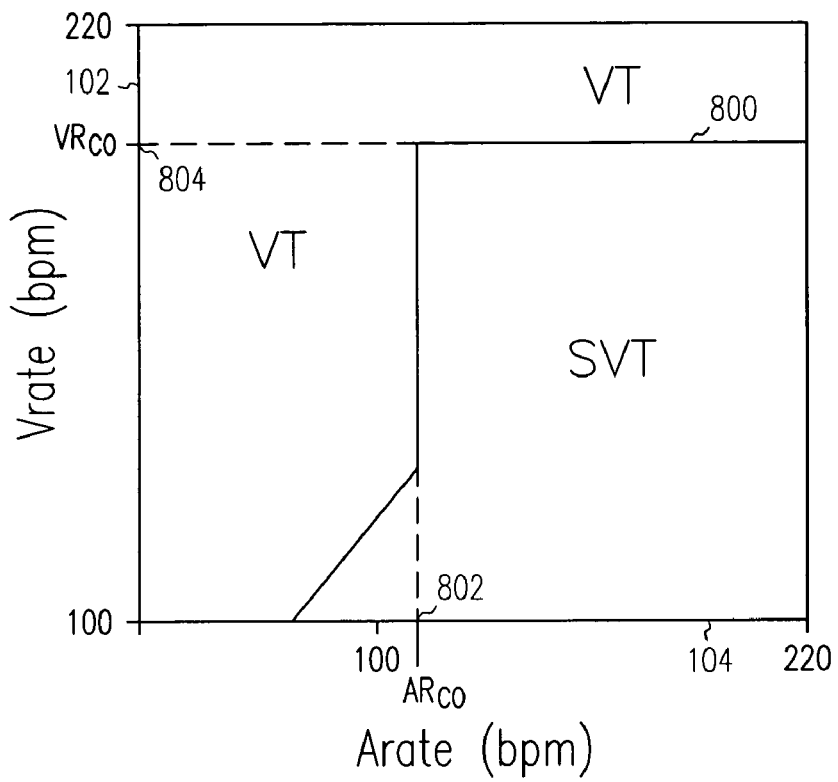
FIG. 8 is a graph illustrating an alternative example in which the rate dependent threshold boundary implements both an atrial rate cutoff and a ventricular rate cutoff.

FIG. 8 is a graph illustrating an alternative example in which the rate dependent threshold boundary 800 implements both an atrial rate cutoff ($AR_{co}$) 802 and a ventricular rate cutoff ($VR_{co}$) 804. In this example, the ventricular rate cutoff has priority over the atrial rate cutoff. That is, if the tachyarrhythmia is observed at a VR that exceeds the ventricular rate cutoff 804, then the tachyarrhythmia is classified as a VT regardless of the AR. Otherwise, if tachyarrhythmia is observed at an AR that exceeds the atrial rate cutoff 802, the tachyarrhythmia is classified as an SVT regardless of the VR. Otherwise, the tachyarrhythmia is classified as a VT if the VR exceeds the AR by the threshold value (i.e., by the distance between the threshold boundary and the AR=VR line).

Although the above examples have been discussed with respect to classifying a tachyarrhythmia as a VT, similar examples also apply to classifying a tachyarrhythmia as SVT. In one example, the above described techniques may classify as an SVT any tacharrhythmia that is not deemed a VT. In another example, however, the SVT classification uses a separate test. That separate test may be individually tailored to classify the SVT with greater specificity than would be the case if a single test were used to classify a detected arrhythmia as a VT or an SVT.

Figure 9:
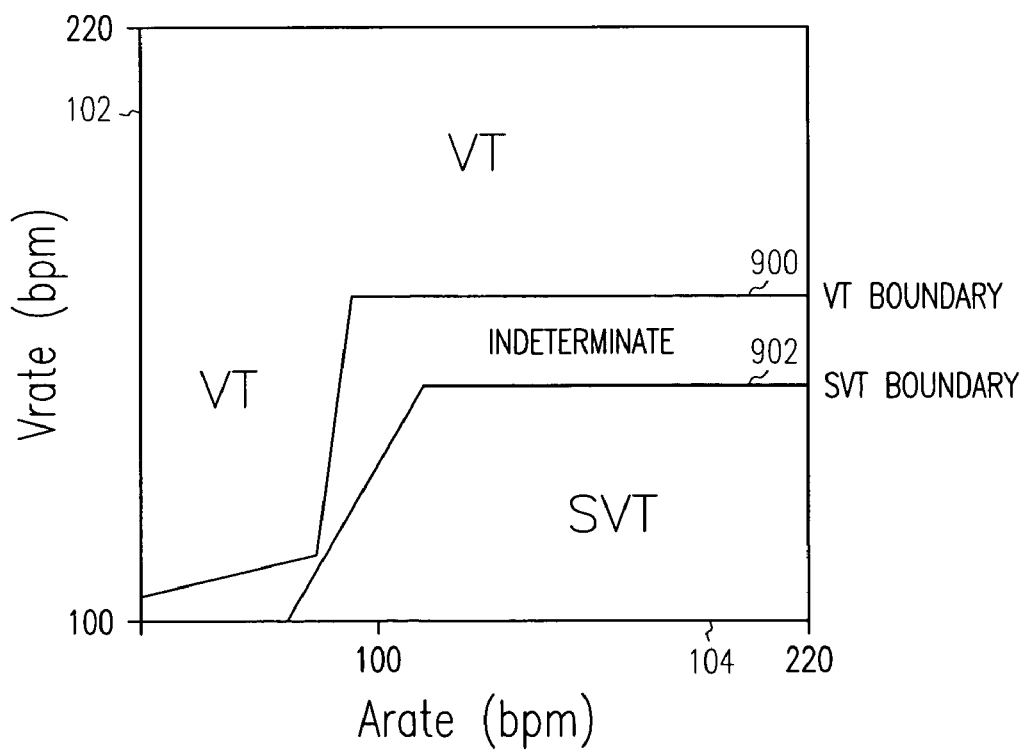
FIG. 9 is a graph illustrating an example of a rate dependent VT threshold boundary that is separate or different from the rate dependent SVT threshold boundary.

FIG. 9 is a graph illustrating an example of a rate dependent VT threshold boundary 900 that is separate or different from the rate dependent SVT threshold boundary 902. Because using separate boundaries may result in one or more indeterminate regions (either because the tachyarrhythmia is not classified as either a VT or an SVT, or because the tachyarrhythmia is classified as both a VT or SVT), it may be desirable to use the rate dependent threshold techniques described in this document together with one or more other VT/SVT discrimination techniques. Examples of other VT/SVT discrimination techniques include, by way of example, but not by way of limitation, stability, onset, vector timing, or correlation. The particular classification may be made by weighting or otherwise combining the results of more than one discrimination technique, either for the case of separate VT and SVT threshold boundaries as shown in FIG. 9, or for the other examples such as illustrated in FIGS. 1–8. Moreover, the examples shown in FIGS. 1–9 or elsewhere in this document can be used in combination with each other, or in combination with other VT/SVT discrimination techniques.

Figure 10:
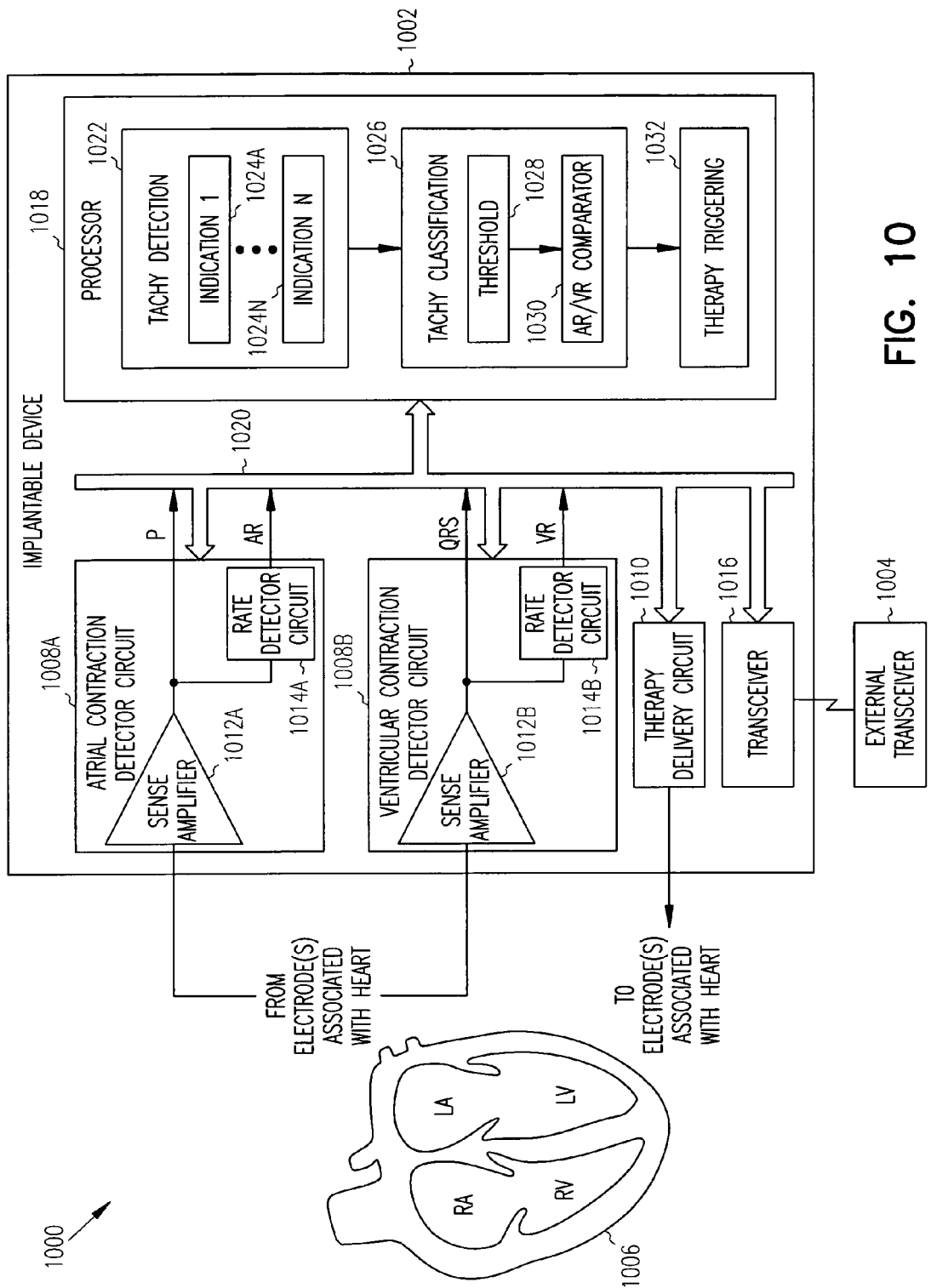
FIG. 10 is a block diagram illustrating generally one example of a system providing VT/SVT discrimination.

FIG. 10 is a block diagram illustrating generally one example of a system 1000 providing the VT/SVT discrimination techniques described above. In FIG. 10, the system 1000 includes a cardiac rhythm management (CRM) or other implantable device 1002, which may be accompanied by an external transceiver 1004 of an external programmer, a repeater, or other communication device. The implantable device 1002 is coupled to a patient's heart 1006, such as by one or more intravascular or other leads carrying electrodes or the like for sensing heart signals or providing anti-tachyarrhythmia or other therapy to the heart 1006.

In the example of FIG. 10, the implantable device 1002 includes an atrial heart contraction detector circuit 1008A and a ventricular heart contraction detector circuit 1008B. The heart contraction detector circuits 1008A–B detect heart contractions associated with a respective atrium or ventricle of the heart 1006, such as by sensing the intrinsic electrical heart signals from the heart chamber or by detecting triggering signals from contraction-evoking pulses delivered by a therapy circuit 1010 to the heart chamber.

The atrial contraction detector circuit 1008A includes a sense amplifier 1012A providing an output signal representative of the intrinsic atrial heart signal. This output signal includes electrical depolarizations (called "P-waves") representing successive atrial heart contractions. The output signal is received by an atrial rate detector circuit 1014A, which measures a time between successive atrial heart contractions to provide an output indication of the atrial rate ("AR").

Similarly, the ventricular contraction detector circuit 1008B includes a sense amplifier 1012B providing an output signal representative of the intrinsic ventricular heart signal. This output signal includes electrical depolarizations (called "QRS-complexes") representing successive ventricular heart contractions. The output signal is received by a ventricular rate detector circuit 1014B, which measures a time between successive ventricular heart contractions to provide an output indication of the ventricular rate ("VR").

The therapy delivery circuit 1010 typically includes one or more of: a pace pulse delivery circuit, an anti-tachyarrhythmia therapy circuit, a cardiac resynchronization therapy circuit, a cardiac contractility modulation (CCM) circuit, or any other therapy delivery circuit. The anti-tachyarrhythmia therapy circuit typically includes at least one defibrillation circuit or anti-tachyarrhythmia pacing (ATP) circuit or the like.

In the example of FIG. 10, the implantable device 1002 also includes a transceiver 1016 for wirelessly communicating with the external transceiver 1004. The implantable device 1002 also includes a processor 1018. The processor 1018 is coupled to the other circuits of the implantable device 1002 by at least one bus 1020 or the like. The processor 1018 is implemented as any controller or other circuit that is capable of sequencing through various control states such as, for example, by using a digital microprocessor having executable instructions stored in an associated instruction memory circuit, a microsequencer, or a state machine.

In the example of FIG. 10, the processor 1018 includes a tachyarrhythmia detection circuit 1022. The tachyarrhythmia detection circuit 1022 processes signals received from the atrial contraction detector circuit 1008A or the ventricular contraction detector circuit 1008B. In response, the tachyarrhythmia detection circuit 1022 provides one or more indications 1024A–N that a tachyarrhythmia is present. As one illustrative example, an a first indication 1024A (sometimes referred to as an "Onset" indication) deems three consecutive "fast" (for example, at a rate greater than about 165 bpm) intervals between contractions of the same heart chamber as providing a first indication 1024 of an onset of a tachyarrhythmia.

In this same example, if the first indication 1024A indicates an onset of a tachyarrhythmia, then this triggers a second test for a second indication 1024N (sometimes referred to as a "Duration" indication). This second test looks for the presence of three of ten fast intervals occuring during a time period referred to as the "duration" period. If this condition is met, then the second indication 1024N of a tachyarrhythmia is also present. In this way, a desired number of tachyarrhythmia indications can be used conjunctively to increase the specificity of a tachyarrhythmia detection before anti-tachyarrhythmia therapy is delivered.

The example of FIG. 10 also includes a tachyarrhythmia classification circuit 1026. In one example, the tachyarrhythmia classification circuit 1026 performs the VT/SVT discrimination, such as discussed above. Therefore, in one example, the tachyarrhythmia classification circuit 1026 includes a rate-dependent threshold 1028 (such as discussed above). The rate-dependent threshold 1028 is provided to a comparator 1030 that compares atrial and ventricular rates, using the rate-dependent threshold, to classify the tachyarrhythmia as VT or SVT. The rate-dependent threshold

1028 can be stored in one or more memory locations in various different forms, such as an equation, a lookup table, or in any other desired form.

The comparator 1030 compares the atrial rate and the ventricular rate using the rate-dependent threshold 1028. In one example of classifying a tachyarrhythmia as VT, the tachyarrhythmia classification circuit uses a ventricular rate (or atrial rate) received from the ventricular rate detector circuit 1014B (or the atrial rate detector 1014A) as an index into a rate-dependent function that yields a threshold value for comparing AR and VR. If VR exceeds AR by at least the threshold value, then the tachyarrhythmia classification circuit deems the tachyarrhythmia to be a VT instead of an SVT.

In the example of FIG. 10, the processor 1018 also includes a therapy triggering circuit 1032 that triggers an appropriate anti-tachyarrhythmia therapy in response to the tachyarrhythmia detection indication(s) from the tachyarrhythmia detection circuit 1022 and the tachyarrhythmia classification from the tachyarrhythmia classification circuit 1026. As an illustrative example, a detected tachyarrhythmia that is classified as VT may be treated with a defibrillation shock, while a detected tachyarrhythmia that is classified as an SVT may be treated by an anti-tachyarrhythmia pacing (ATP) pulse sequence. In general, there may be many different therapy responses, with the particular therapy response depending on the tachyarrhythmia classification or the particular tachyarrhythmia detection indication(s) that are present.

Figure 11:
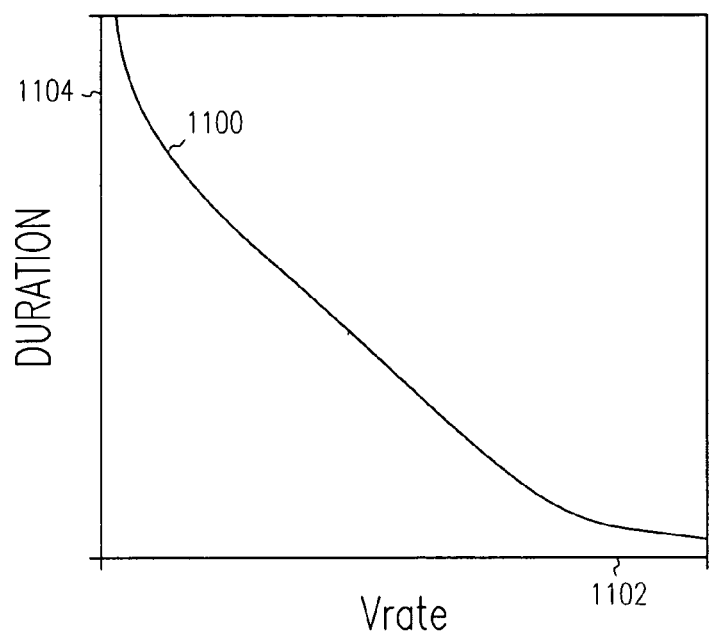
FIG. 11 is a graph of a duration interval function, in which the y-axis represents the value of the duration interval and the x-axis represents a ventricular rate.

In one example, at least one of the tachyarrhythmia detection indications 1024A–N is rate-dependent. In one example, the "duration" time interval discussed above is also rate dependent, as illustrated conceptually in FIG. 11. FIG. 11 is a graph of a duration interval function 1100, in which the y-axis 1102 represents the value of the duration interval and the x-axis 1104 represents a ventricular rate. In this example, the duration interval function 1100 automatically substantially continuously decreases monotonically with increasing ventricular rate. In the example illustrated in FIG. 11, a test for "X" of "Y" fast intervals is carried out over a shorter duration interval period at a higher ventricular rate than for a lower ventricular rate. The actual numbers for "X" and "Y" may also typically vary as a function of the ventricular rate. The example discussed earlier tested for X=6 of Y=10 fast intervals occurring during a duration period (e.g., 2.5 seconds). In one rate-dependent duration interval period example, this duration period corresponds to a VR=160 bpm. As one illustrative example, at a lower VR=130, a duration period of about 5 seconds is used, and the corresponding tachyarrhythmia detection test looks for X=12 of Y=20 fast R—R intervals between successive ventricular contractions. Continuing with this illustrative example, at a higher VR=240, a duration period of about 1 second is used, and the corresponding tachyarrhythmia detection test looks for X=3 of Y=5 fast R—R intervals. These values are provided for illustrative purposes only, the exact values may be programmed as desired. In one example, such programming is performed by the manufacturer, so that the physician need not program various durations corresponding to various ventricular rates. Such automaticity increases the ease of use of the implantable device 1002.

Figure 12:
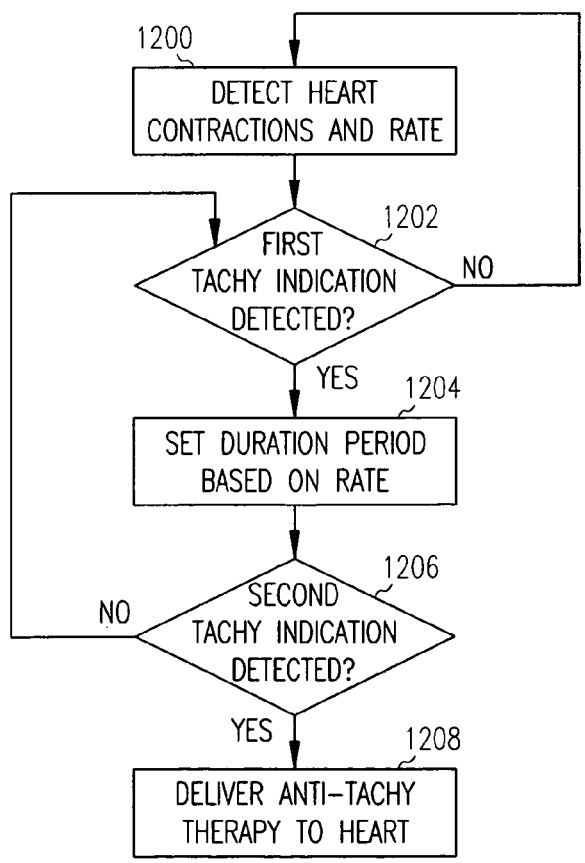
FIG. 12 is a flow chart illustrating generally one example of using at least one rate-dependent tachyarrhythmia detection criterion.

FIG. 12 is a flow chart illustrating generally one example of using at least one rate-dependent tachyarrhythmia detection criterion. In the example of FIG. 12, at 1200, heart contractions and heart rate are detected. In one example this includes detecting ventricular heart contractions and ventricular heart rate. At 1202, a first test is performed to determine if a tachyarrhythmia is present. In one illustrative example, if three consecutive fast intervals between successive ventricular contractions is detected, an "onset" of a tachyarrhythmia is deemed present, and process flow continues at 1204; otherwise process flow returns to 1200. At 1204, a "duration period" parameter of a second tachyarrhythmia detection test corresponding to a particular heart rate is established. In one example, a substantially continuously decreasing duration vs. ventricular rate function, as illustrated in FIG. 11, is used to automatically set the duration period at 1204. At 1206, a second test is performed to confirm that the tachyarrhythmia is present. In one illustrative example, if three of ten fast intervals (intervals shorter than a threshold interval value) between successive ventricular contractions are detected during the duration period that was selected using the ventricular rate, then the tachyarrhythmia is deemed to be present. In a further example, the second test determines if X of Y fast intervals is present during the automatically selected duration period, where X or Y is also selected using the rate. If the second test deems a tachyarrhythmia to be present, then process flow continues to 1208, and anti-tachyarrhythmia therapy is delivered to the heart.

In the above example, the rate-dependent duration period can alternatively be used as a single tachyarrhythmia detection test (e.g., without a first tachyarrhythmia detection criterion, such as the onset), or could be used in conjunction with one or more additional tachyarrhythmia detection criteria. Also, the above example could also be used in conjunction with a tachyarrhythmia classification before anti-tachyarrhythmia therapy is delivered. This permits the particular anti-tachyarrhythmia therapy to be tailored using the classification or the tachyarrhythmia detection indication(s). The rate-dependent duration period can be used with a rate-dependent threshold for arrhythmia detection, as discussed above, or with a rate-independent threshold for arrhythmia detection, if desired.

Figure 13:
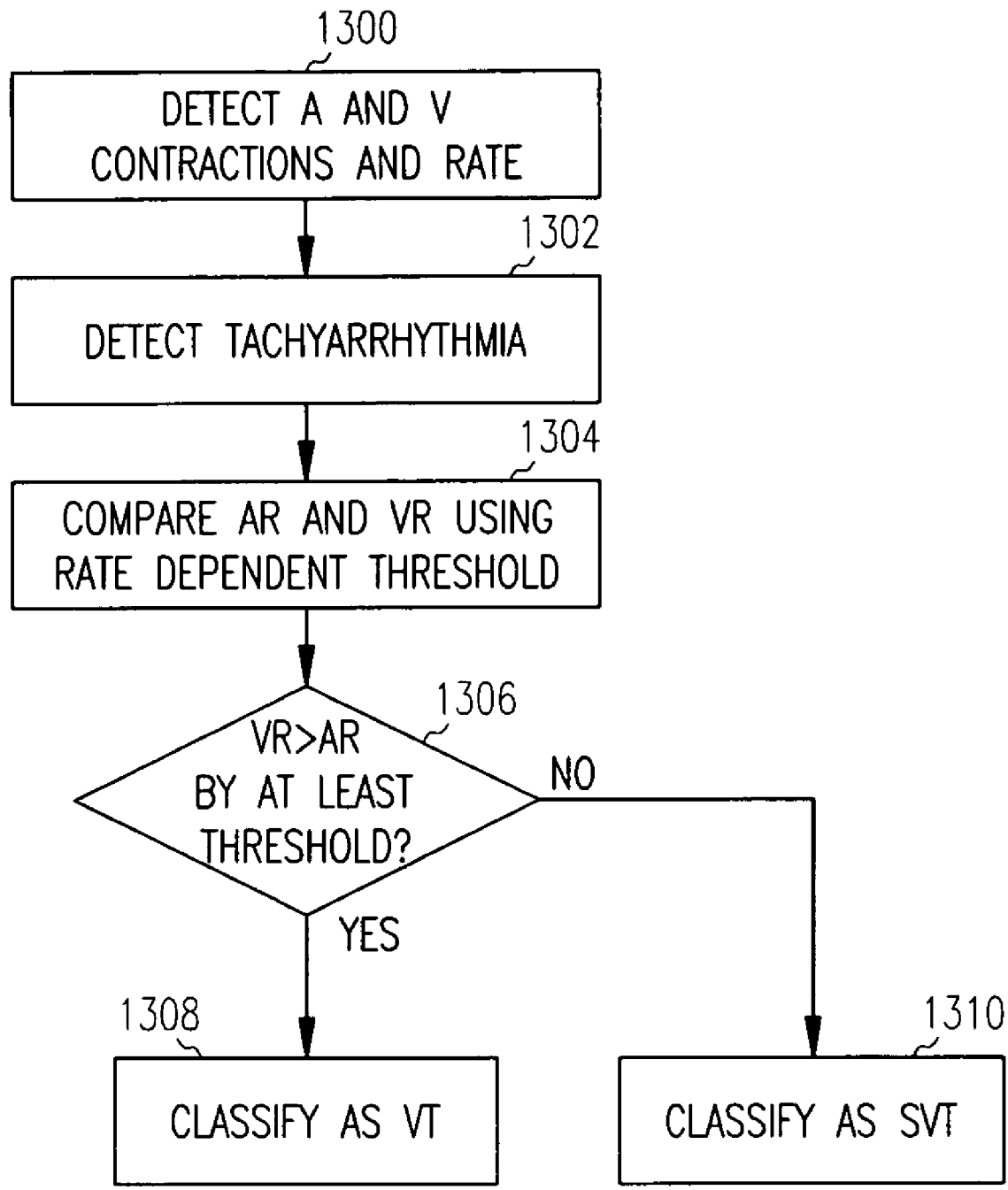
FIG. 13 is a flow chart illustrating generally one example of tachyarrhythmia classification.

FIG. 13 is a flow chart illustrating generally one example of tachyarrhythmia classification. In the example of FIG. 13, at 1300, atrial and ventricular contractions and rate are detected. At 1300, atrial and ventricular contractions and corresponding rates are detected. At 1302, a tachyarrhythmia is detected, such as by using one or more tachyarrhythmia detection criteria (e.g., onset test, duration test, etc.), examples of which are discussed above. At 1304, atrial rate and ventricular rate are compared using a bilinear, piecewise linear, curvilinear or other rate-dependent threshold, as discussed above. The particular threshold value used for the comparison is selected using one of ventricular rate or atrial rate. At 1306, if VR exceeds AR by the threshold value corresponding to the observed heart rate, then at 1308, the tachyarrhythmia is classified as a VT. Otherwise, at 1310, the tachyarrhythmia is either classified as an SVT, or a separate SVT classification routine is initiated at 1310. In one example, after the classification is made, an anti-tachyarrhythmia therapy is then delivered. In another example, after the classification is made, one or more classification-specific tachyarrhythmia detection criteria is then applied to further enhance the specificity of the detection. In yet a further example, the anti-tachyarrhythmia therapy is tailored using one of the classification or the tachyarrhythmia detection criteria.

Figure 14:
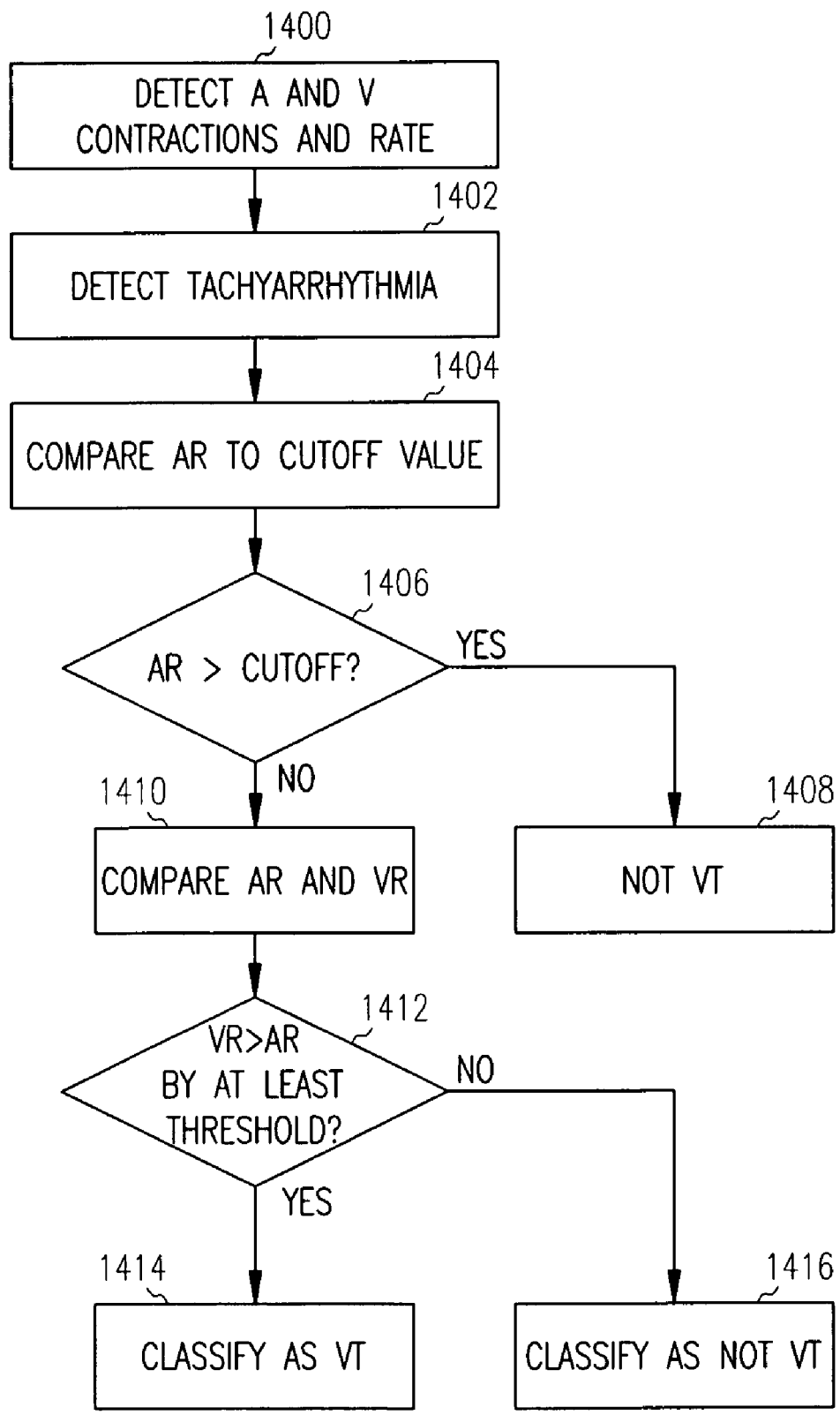
FIG. 14 is a flow chart illustrating generally one example of a technique of classifying a tachyarrhythmia using a rate cutoff value.

FIG. 14 is a flow chart illustrating generally one example of a technique of classifying a tachyarrhythmia using a rate cutoff value. In the example of FIG. 14, at 1400, atrial and ventricular contractions and rates are detected. At 1402, a tachyarrhythmia is detected using one or more tachyarrhythmia detection indications. In one example, at least one of these tachyarrhythmia detection indications uses a rate-dependent duration period, as discussed above. At 1404, the atrial rate is compared to a cutoff value. At 1406, if the atrial rate exceeds the cutoff value, then, at 1408, the detected arrhythmia is deemed not a VT. Otherwise, at 1410, atrial rate and ventricular rates are compared. In one example, this comparison includes using a bilinear, piecewise linear, curvilinear, or other rate-dependent threshold value. In another example, this comparison includes using a rate-independent threshold value. At 1412, if the ventricular rate exceeds the atrial rate by at least the threshold value, then, at 1414, the tachyarrhythmia is classified as a VT. Otherwise, at 1416, the tachyarrhythmia is classified as not VT. In one example, after the classification is made, an anti-tachyarrhythmia therapy is then delivered. In another example, after the classification is made, one or more classification-specific tachyarrhythmia detection criteria is then applied to further enhance the specificity of the detection. In yet a further example, the anti-tachyarrhythmia therapy is tailored using one of the classification or the tachyarrhythmia detection criteria. Alternatively, the example illustrated in FIG. 14 is used to implement a ventricular rate cutoff instead of an atrial rate cutoff, in which a ventricular rate exceeding the corresponding ventricular rate cutoff results in the detected tachyarrhythmia being classified as a VT.

Figure 15:
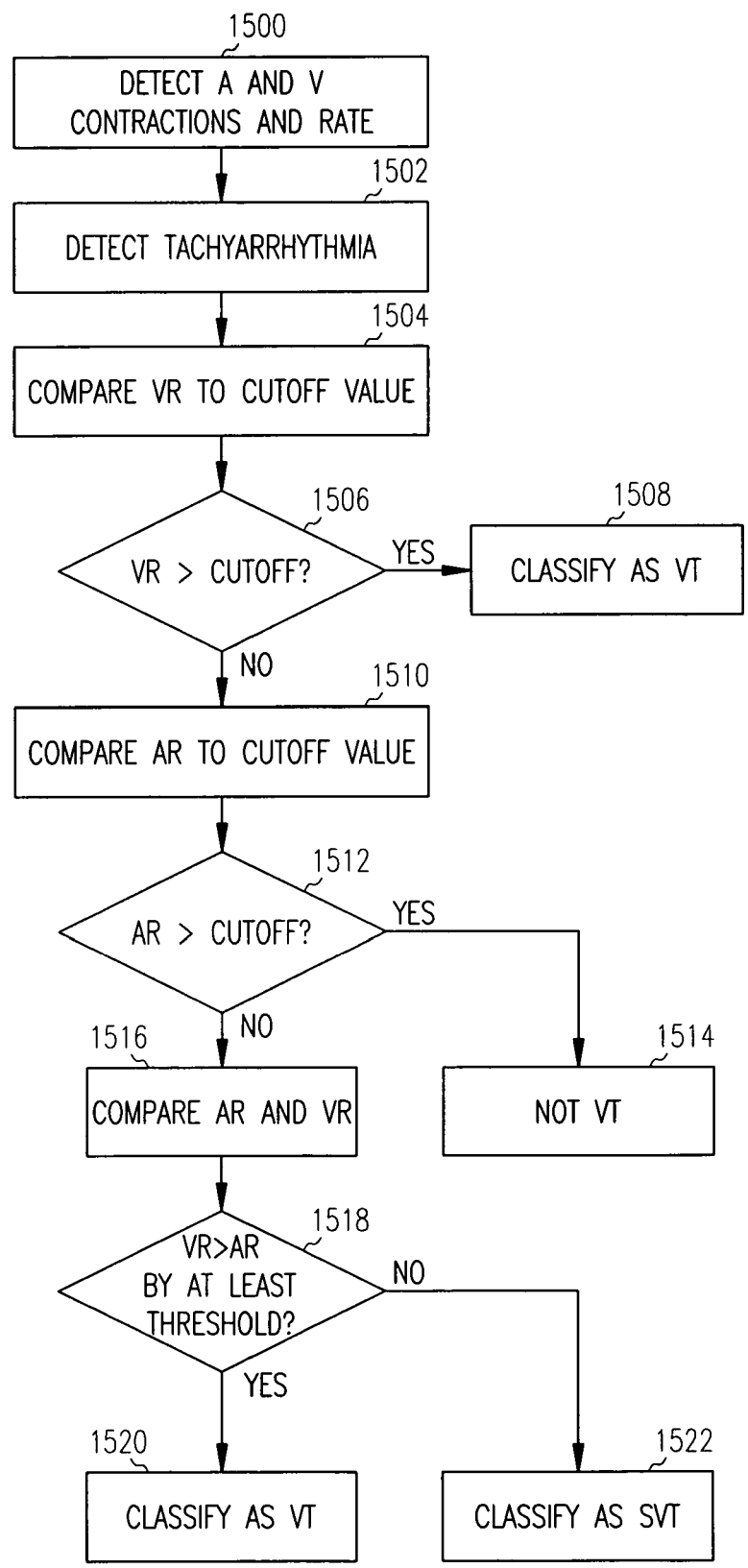
FIG. 15 is a flow chart illustrating generally an example of a technique of classifying a tachyarrhythmia using ventricular and atrial rate cutoff values.

FIG. 15 is a flow chart illustrating generally an example of a technique of classifying a tachyarrhythmia using ventricular and atrial rate cutoff values. In the example of FIG. 15, at 1500, atrial and ventricular contractions and rates are detected. At 1502, a tachyarrhythmia is detected using one or more tachyarrhythmia detection indications. In one example, at least one such tachyarrhythmia detection indication uses a rate-dependent duration period, as discussed above. At 1504, the ventricular rate is compared to a cutoff value. At 1506, if the ventricular rate exceeds the cutoff value, then, at 1508, the detected arrhythmia is deemed a VT. Otherwise, at 1510, the atrial rate is compared to a cutoff value. At 1512, if the atrial rate exceeds the cutoff value, then, at 1514, the detected arrhythmia is deemed not a VT. Otherwise, at 1516, atrial rate and ventricular rates are compared. In one example, this comparison includes using a bilinear, piecewise linear, curvilinear, or other rate-dependent threshold value, as discussed above. In another example, this comparison includes using a rate-independent threshold value. At 1518, if the ventricular rate exceeds the atrial rate by at least the threshold value, then, at 1520, the tachyarrhythmia is classified as a VT. Otherwise, at 1522, the tachyarrhythmia is classified as not VT. In one example, after the classification is made, an anti-tachyarrhythmia therapy is then delivered. In another example, after the classification is made, one or more classification-specific tachyarrhythmia detection criteria is then applied to further enhance the specificity of the detection. In yet a further example, the anti-tachyarrhythmia therapy is tailored using one of the classification or the tachyarrhythmia detection criteria.

The above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A system comprising:
    an atrial contraction detector circuit, including an atrial rate detector circuit to detect an atrial rate between atrial contractions of a heart;
    a ventricular contraction detector circuit, including a ventricular rate detector circuit to detect a ventricular rate between ventricular contractions of the heart; and
    a processor, coupled to the atrial and ventricular rate detector circuits, the processor including:
        a tachyarrhythmia detection module; and
        a tachyarrhythmia classification module including a first comparator for determining if the ventricular rate exceeds the atrial rate by a threshold value, in which the threshold value varies as a function of at least one of the atrial rate and the ventricular rate, and in which if the ventricular rate exceeds the atrial rate by the threshold value corresponding to the at least one of the atrial rate and the ventricular rate, then deeming the tachyarrhythmia to be a ventricular tachyarrhythmia.

2. The system of claim 1, comprising an anti-tachyarrhythmia therapy circuit, coupled to the processor, and delivering an anti-tachyarrhythmia therapy to the ventricle if the tachyarrhythmia is a ventricular tachyarrhythmia.

3. The system of claim 1, in which the threshold value is larger at a lower value of the ventricular rate than at a higher value of the ventricular rate.

4. The system of claim 1, in which the threshold value is a bilinear mapping between the atrial and ventricular rates.

5. The system of claim 1, in which the threshold value is a piecewise linear mapping between the atrial and ventricular rates.

6. The system of claim 1, in which the threshold value is a curvilinear mapping between the atrial and ventricular rates.

7. The system of claim 1, in which if the atrial rate exceeds a cutoff value, then the tachyarrhythmia classification module deems the tachyarrhythmia to be an atrial tachyarrhythmia and not a ventricular tachyarrhythmia, without regard to whether the ventricular rate exceeds the atrial rate by the threshold value.

8. A method comprising:
    detecting atrial heart contractions and an atrial rate between the atrial heart contractions of an atrium of a heart;
    detecting ventricular heart contractions and a ventricular rate between the ventricular heart contractions of a ventricle of the heart;
    detecting a tachyarrhythmia;
    determining if the ventricular rate exceeds the atrial rate by a threshold value, in which the threshold value varies as a function of at least one of the atrial rate and the ventricular rate; and
    if the ventricular rate exceeds the atrial rate by the threshold value corresponding to the at least one of the atrial rate and the ventricular rate, then deeming the tachyarrhythmia to be a ventricular tachyarrhythmia.

9. The method of claim 8, further comprising delivering an anti-tachyarrhythmia therapy to the ventricle if the tachyarrhythmia is a ventricular tachyarrhythmia.

10. The method of claim 8, in which the threshold value is larger at a lower value of the ventricular rate than at a higher value of the ventricular rate.

11. The method of claim 8, in which the threshold value is a bilinear mapping between the atrial and ventricular rates.

12. The method of claim 8, in which the threshold value is a piecewise linear mapping between the atrial and ventricular rates.

13. The method of claim 8, in which the threshold value is a curvilinear mapping between the atrial and ventricular rates.

14. The method of claim 8, in which if the atrial rate exceeds a cutoff value, then deeming the tachyarrhythmia to be an atrial tachyarrhythmia and not a ventricular tachyarrhythmia, regardless of whether the ventricular rate exceeds the atrial rate by the threshold value.

15. A system comprising:
an atrial contraction detector circuit, including an atrial rate detector circuit to detect an atrial rate between atrial contractions of a heart;
a ventricular contraction detector circuit, including a ventricular rate detector circuit to detect a ventricular rate between ventricular contractions of the heart;
an anti-tachyarrhythmia therapy circuit; and
a processor, coupled to the atrial and ventricular rate detector circuits and the anti-tachyarrhythmia therapy circuit, the processor including:
a tachyarrhythmia detection module; and
a tachyarrhythmia therapy module, including a first comparator for determining if the ventricular rate exceeds the atrial rate by a threshold value, in which the threshold value varies as a function of at least one of the atrial rate and the ventricular rate, and triggering the delivering an anti-tachyarrhythmia therapy to the ventricle by the anti-tachyarrhythmia therapy circuit only if the ventricular rate exceeds the atrial rate by the threshold value corresponding to the at least one of the atrial rate and the ventricular rate.

16. The system of claim 15, in which the triggering the delivering the anti-tachyarrhythmia therapy to the ventricle also requires at least one other ventricular tachyarrhythmia therapy delivery criterion to be met before the delivering the anti-tachyarrhythmia therapy to the ventricle.

17. The system of claim 15, in which the threshold value is larger at a lower value of the ventricular rate than at a higher value of the ventricular rate.

18. The system of claim 15, in which the threshold value is a bilinear mapping between the atrial and ventricular rates.

19. The system of claim 15, in which the threshold value is a piecewise linear mapping between the atrial and ventricular rates.

20. The system of claim 15, in which the threshold value is a curvilinear mapping between the atrial and ventricular rates.

21. The system of claim 15, in which if the atrial rate exceeds a cutoff value, then the tachyarrhythmia classification module deems the tachyarrhythmia to be an atrial tachyarrhythmia and not a ventricular tachyarrhythmia, without regard to whether the ventricular rate exceeds the atrial rate by the threshold value.

22. A method comprising:
detecting atrial heart contractions and an atrial rate between the atrial heart contractions of an atrium of a heart;
detecting ventricular heart contractions and a ventricular rate between the ventricular heart contractions of a ventricle of the heart;
detecting a tachyarrhythmia;
determining if the ventricular rate exceeds the atrial rate by a threshold value, in which the threshold value varies as a function of at least one of the atrial rate and the ventricular rate; and
delivering an anti-tachyarrhythmia therapy to the ventricle only if the ventricular rate exceeds the atrial rate by the threshold value corresponding to the at least one of the atrial rate and the ventricular rate.

23. The method of claim 22, in which the delivering the anti-tachyarrhythmia therapy to the ventricle includes also requires at least one other ventricular tachyarrhythmia therapy delivery criterion to be met before the delivering the anti-tachyarrhythmia therapy to the ventricle.

24. The method of claim 22, in which the threshold value is larger at a lower value of the ventricular rate than at a higher value of the ventricular rate.

25. The method of claim 22, in which the threshold value is a bilinear mapping between the atrial and ventricular rates.

26. The method of claim 22, in which the threshold value is a piecewise linear mapping between the atrial and ventricular rates.

27. The method of claim 22, in which the threshold value is a curvilinear mapping between the atrial and ventricular rates.

28. The method of claim 22, in which if the atrial rate exceeds a cutoff value, then deeming the tachyarrhythmia to be an atrial tachyarrhythmia and not a ventricular tachyarrhythmia, regardless of whether the ventricular rate exceeds the atrial rate by the threshold value.

29. A system comprising:
an atrial contraction detector circuit, including an atrial rate detector circuit to detect an atrial rate between atrial contractions of a heart;
a ventricular contraction detector circuit, including a ventricular rate detector circuit to detect a ventricular rate between ventricular contractions of the heart; and
a processor, coupled to the atrial and ventricular rate detector circuits, the processor including:
a tachyarrhythmia detection module; and
a tachyarrhythmia classification module, including a first comparator for classifying a tachyarrhythmia as an atrial tachyarrhythmia if an atrial rate exceeds an atrial rate cutoff value, and including a second comparator for otherwise determining if the ventricular rate exceeds the atrial rate by at least a threshold value, and in which if the ventricular rate exceeds the atrial rate by at least a threshold value, then deeming the tachyarrhythmia to be a ventricular tachyarrhythmia unless the atrial rate exceeds the atrial rate cutoff value, wherein the threshold value varies as a function of at least one of the atrial rate and ventricular rate.

30. The system of claim 29, further comprising an anti-tachyarrhythmia therapy circuit for delivering an anti-tachyarrhythmia therapy to the ventricle if the tachyarrhythmia is a ventricular tachyarrhythmia.

31. The system of claim 29, in which the threshold value is a bilinear mapping between atrial and ventricular rate.

32. The system of claim 29, in which the threshold value is a piecewise linear mapping between atrial and ventricular rate.

33. A method comprising:
 detecting atrial heart contractions and an atrial rate between the atrial heart contractions of an atrium of a heart;
 detecting ventricular heart contractions and a ventricular rate between the ventricular heart contractions of a ventricle of the heart;
 detecting a tachyarrhythmia; and
 if the atrial rate exceeds a cutoff value, then deeming the tachyarrhythmia to be an atrial tachyarrhythmia and not a ventricular tachyarrhythmia, and otherwise determining if the ventricular rate exceeds the atrial rate by at least a threshold value, and if the ventricular rate exceeds the atrial rate by at least a threshold value, then deeming the tachyarrhythmia to be a ventricular tachyarrhythmia, wherein the threshold value varies as a function of at least one of the atrial rate and the ventricular rate.

34. The method of claim 33, further comprising delivering an anti-tachyarrhythmia therapy to the ventricle if the tachyarrhythmia is a ventricular tachyarrhythmia.

35. The method of claim 33, in which the threshold value is a bilinear mapping between atrial and ventricular rate.

36. The method of claim 33, in which the threshold value is a piecewise linear mapping between atrial and ventricular rate.

37. A system comprising:
 an atrial contraction detector circuit, including an atrial rate detector circuit to detect an atrial rate between atrial contractions of a heart;
 a ventricular contraction detector circuit, including a ventricular rate detector circuit to detect a ventricular rate between ventricular contractions of the heart;
 an anti-tachyarrhythmia therapy circuit; and
 a processor, coupled to the atrial and ventricular rate detector circuits and the anti-tachyarrhythmia therapy circuit, the processor including:
  a tachyarrhythmia detection module; and
  a tachyarrhythmia therapy module, including a first comparator for classifying a tachyarrhythmia as an atrial tachyarrhythmia if an atrial rate exceeds an atrial rate cutoff value, and including a second comparator for otherwise determining if the ventricular rate exceeds the atrial rate by at least a threshold value, and triggering the delivering of anti-tachyarrhythmia therapy to the ventricle only if the ventricular rate exceeds the atrial rate by at least the threshold value and the atrial rate is below the atrial rate cutoff value, wherein the threshold value varies as a function of at least one of the atrial rate and ventricular rate.

38. The system of claim 37, in which the triggering the delivering the anti-tachyarrhythmia therapy to the ventricle also requires at least one other ventricular tachyarrhythmia therapy delivery criterion to be met before the delivering the anti-tachyarrhythmia therapy to the ventricle.

39. The system of claim 37, in which the threshold value is a bilinear mapping between atrial and ventricular rate.

40. The system of claim 37, in which the threshold value is a piecewise linear mapping between atrial and ventricular rate.

41. A method comprising:
 detecting atrial heart contractions and an atrial rate between the atrial heart contractions of an atrium of a heart;
 detecting ventricular heart contractions and a ventricular rate between the ventricular heart contractions of a ventricle of the heart;
 detecting a tachyarrhythmia; and
 triggering a delivering of anti-tachyarrhythmia therapy to the ventricle only if the atrial rate is less than a cutoff value and the ventricular rate exceeds the atrial rate by at least a threshold value, wherein the threshold value varies as a function of at least one atrial rate and the ventricular rate.

42. The method of claim 41, in which the triggering the delivering the anti-tachyarrhythmia therapy to the ventricle also requires at least one other ventricular tachyarrhythmia therapy delivery criterion to be met before the delivering the anti-tachyarrhythmia therapy to the ventricle.

43. The method of claim 41, in which the threshold value is a bilinear mapping between atrial and ventricular rate.

44. The method of claim 41, in which the threshold value is a piecewise linear mapping between atrial and ventricular rate.

45. A system comprising:
 a ventricular contraction detector circuit, including a ventricular rate detector circuit to detect a ventricular rate between ventricular contractions of a heart;
 an anti-tachyarrhythmia therapy circuit; and
 a processor, coupled to the atrial and ventricular rate detector circuits and the anti-tachyarrhythmia therapy circuit, the processor including:
  a tachyarrhythmia detection module; and
  a tachyarrhythmia therapy module, including an initial tachyarrhythmia detection indication and a duration timer measuring a subsequent first duration period that is substantially continuously decreasing monotonically with increasing ventricular rate, and triggering a delivering of ventricular anti-tachyarrhythmia therapy only if the initial tachyarrhythmia indication is detected and during the subsequent first duration period, a second tachyarrhythmia indication is detected using at least one tachyarrhythmia detection criterion.

46. The system of claim 45, in which the initial tachyarrhythmia indication comprises a comparator for detecting a fixed number of heart contractions at a rate that exceeds a first rate cutoff value.

47. The system of claim 45, in which the second tachyarrhythmia indication includes a comparator for monitoring, during the first duration period, for a first number of fast ventricular contractions out of a second number of ventricular contractions observed during the first duration period.

48. A method comprising:
 detecting ventricular heart contractions and a ventricular rate between the ventricular heart contractions of a ventricle of a heart;
 detecting an initial tachyarrhythmia indication;
 if the initial tachyarrhythmia indication is detected, then detecting, during a first duration period, a second tachyarrhythmia indication using at least one tachyarrhythmia criterion, the first duration period substantially continuously decreasing monotonically with increasing ventricular rate; and if the second tachyarrhythmia indication is detected, then delivering an anti-tachyarrhythmia therapy to the heart.

49. The method of claim 48, in which the detecting the initial tachyarrhythmia indication comprises detecting a fixed number of heart contractions at a rate that exceeds a first rate cutoff value.

50. The method of claim 48, in which the detecting the second tachyarrhythmia indication includes monitoring, during the first duration period, for a first number of fast ventricular contractions out of a second number of ventricular contractions observed during the first duration period.

* * * * *